(12) United States Patent
Grant (10) Patent No.: US 11,597,904 B2
(45) Date of Patent: Mar. 7, 2023

(54) LIQUID FILTRATION SYSTEM WITH INTEGRATED BLEED FUNCTION

(71) Applicant: The Automation Partnership (Cambridge) Limited, Royston (GB)

(72) Inventor: Paul Grant, Suffolk (GB)

(73) Assignee: The Automation Partnership (Cambridge) Limited, Royston (GB)

( * ) Notice: Subject to any disclaimer, the term of this patent is extended or adjusted under 35 U.S.C. 154(b) by 364 days.

(21) Appl. No.: 16/312,182

(22) PCT Filed: Jul. 18, 2017

(86) PCT No.: PCT/EP2017/068165
§ 371 (c)(1),
(2) Date: Dec. 20, 2018

(87) PCT Pub. No.: WO2018/015405
PCT Pub. Date: Jan. 25, 2018

(65) Prior Publication Data
US 2020/0181554 A1  Jun. 11, 2020

(30) Foreign Application Priority Data
Jul. 19, 2016 (EP) .................................... 16180185

(51) Int. Cl.
*C12M 1/00* (2006.01)
*B01D 35/26* (2006.01)
(Continued)

(52) U.S. Cl.
CPC ............. *C12M 29/10* (2013.01); *B01D 35/26* (2013.01); *B01D 37/045* (2013.01);
(Continued)

(58) Field of Classification Search
CPC ...... C12M 29/10; C12M 29/04; C12M 29/18; C12M 41/36; C12M 41/40; C12M 41/44; C12M 41/46; B01D 35/26; B01D 37/046
(Continued)

(56) References Cited

U.S. PATENT DOCUMENTS 3,472,765 A * 10/1969 Okey .................... C12M 29/18
210/607
2009/0035856 A1 * 2/2009 Galliher ................ C12M 29/10
435/383
(Continued)

FOREIGN PATENT DOCUMENTS

CN  101985597 A  3/2011
CN  102071137 A  5/2011
(Continued)

OTHER PUBLICATIONS

International Search Report and Written Opinion for PCT/EP2017/068165, dated Nov. 14, 2017.
(Continued)

*Primary Examiner* — Michael L Hobbs
*Assistant Examiner* — Lenora A Abel
(74) *Attorney, Agent, or Firm* — Klarquist Sparkman, LLP (57) ABSTRACT

A liquid filtration system according to the present invention comprises a bioreactor; a filter configured to filter liquid passing therethrough; a perfusion pump configured to move liquid between the bioreactor and the filter; a liquid line providing fluidic communication between the bioreactor, perfusion pump and filter; and a bleed outlet provided on the liquid line, the bleed outlet configured to provide means to remove liquid selectively from the system under the action of the perfusion pump. With the liquid filtration system according to the present invention, both the filtering and (Continued)

bleed functions may be performed under the action of a single pump, thereby significantly reducing the complexity and cost of the components required.

12 Claims, 5 Drawing Sheets

(51) Int. Cl.
*B01D 37/04* (2006.01)
*C12M 1/34* (2006.01)

(52) U.S. Cl.
CPC ........... *B01D 37/046* (2013.01); *C12M 29/04* (2013.01); *C12M 29/18* (2013.01); *C12M 41/36* (2013.01); *C12M 41/40* (2013.01); *C12M 41/44* (2013.01); *C12M 41/46* (2013.01)

(58) Field of Classification Search
USPC ...................................................... 435/286.5
See application file for complete search history.

(56) References Cited

U.S. PATENT DOCUMENTS

| | | | | |
|---|---|---|---|---|
| 2009/0042253 | A1* | 2/2009 | Hiller | C12P 21/00 435/70.3 |
| 2012/0295289 | A1* | 11/2012 | Zandstra | C12M 41/36 435/7.94 |
| 2014/0093952 | A1 | 4/2014 | Serway | |

FOREIGN PATENT DOCUMENTS

| | | |
|---|---|---|
| CN | 103243027 B | 8/2013 |
| CN | 105586249 B | 5/2016 |
| WO | WO85/01064 | 3/1985 |
| WO | WO2009/006909 | 1/2009 |
| WO | WO 2009/006909 A1 | 1/2009 |
| WO | WO2009/023562 | 2/2009 |

OTHER PUBLICATIONS

Office Action, dated May 6, 2021, issued for corresponding Chinese Patent Application No. 2017800405813, 18 pages (with English translation).

* cited by examiner

LIQUID FILTRATION SYSTEM WITH INTEGRATED BLEED FUNCTION

CROSS REFERENCE TO RELATED APPLICATIONS

This is the U.S. National Stage of International Application No. PCT/EP2017/068165, filed Jul. 18, 2017, which was published in English under PCT Article 21(2), which in turn claims the benefit of European Patent Application No. 16180185.7, filed Jul. 19, 2016, which is incorporated herein in its entirety.

FIELD OF THE INVENTION

The present invention relates to a liquid filtration system for filtering a liquid such as a cell culture held within a bioreactor.

BACKGROUND OF THE INVENTION

Systems for filtering liquids are well known in the art where they take many different forms with the typical function of separating, concentrating or removing constituent elements of a liquid, mixture or suspension. Such systems are employed in the biotechnology and pharmaceutical industries to extract certain biological products such as proteins produced using cell cultures within a bioreactor.

In traditional fed-batch bioreactor systems, cells are cultured in batches whereby cells are inoculated into a fresh medium and the cells rapidly enter a growth phase during which they consume the medium nutrients and waste products accumulate in the culture in addition to the secreted protein of interest. After a certain period of time, the cells transition into a stationary phase followed by a decay phase as the cell culture is depleted. At the end of the run the protein is separated from the cell culture as a batch. An issue with such systems, particularly in the case of animal cell cultures, which typically have lower production rates, is the limited yields of the biological product of interest which may be achieved.

Perfusion bioreactors are a known alternative system in which the cells are kept in culture whilst replenishing the culture media, thereby allowing the maintenance of a high cell concentration over a longer period of time, providing a greater yield of the desired biological product. In order to maintain stable cell culture conditions, filtration is required for clarification, selective removal and concentration of certain constituents of the cell media such that the cell culture may be replenished with fresh media and spent media may be removed.

Typical filtration systems employed in perfusion bioreactors utilise a pump which moves cell culture liquid from a bioreactor through a filter wherein the filtrate, including waste or target products, is removed from the system and the retentate, including live cells, is returned to the bioreactor. Culture media nutrients may then be replenished by a separate system to maintain the cell culture in a steady, equilibrium state. Such prior art devices often employ tangential flow filtration, wherein the majority of the feed flow travels tangentially across the surface of the filter. This system provides a gentle filtration method which does not subject the delicate animal cells to significant forces which might damage the cells. Furthermore the tangential flow of liquid across the filter ensures that deposits in the filter, which might cause a blockage, are washed away during the filtration process, increasing the length of time over which the filtration system may be continually run. Such systems may be arranged such that flow of the liquid is in one direction around a loop, circulating from the bioreactor through the filter and returning to the bioreactor (which will be referred to under the general term "tangential flow filtration" or TFF). Alternatively an arrangement may be used in which only a single connection between the bioreactor and filter is used with the direction of flow alternating such that liquid travel from the bioreactor to the filter and returns to the bioreactor along the same line (referred to as "alternating tangential flow filtration" or ATF).

In such perfusion systems, once the desired cell density has been achieved in the bioreactor vessel, it may be desirable to prevent it rising any higher. In order to provide this function, prior art systems often employ means to reduce the cell density by bleeding cell culture out of the system periodically or at a defined flow rate. A flow rate can be chosen based on the growth rate to limit the cell density to a desired value. Bleeding is typically achieved using a dip tube through which cell culture is removed from the bioreactor under the action of a separate pump such as a peristaltic pump utilised solely for this purpose.

There are several drawbacks to this known bleed pump arrangement. In particular, the addition of a second pump to provide the bleed function increases the cost and complexity of the system. It also increases the degree of manual control required or the level and complexity of automation required to control the bleed function in addition to the usual filtering process. Furthermore, this arrangement requires an additional port in the bioreactor which increases the risk of contamination of the cell culture and increases the number of components which must be sterilised between uses.

There accordingly exists a need for a perfusion filtration system providing means to selectively remove cell culture in order to maintain a desired cell density which is inexpensive and straightforward to implement. It is further desirable for the system to reduce the possibility of contamination present in prior art systems and to reduce the complexity of automation and/or the required degree of manual intervention. It is also desirable to provide a simple bleed system which may be integrated in automated systems and may furthermore be employed in both ATF and TFF modes of operation with little or no adaption of the system.

SUMMARY OF THE INVENTION

The present invention seeks to provide a filtration system which has a simple design with a reduced number and complexity of components suitable to be employed with a single use system. Automation of the components should also be straightforward to reduce the degree of manual intervention required and remove the need for complex control systems. It is a further important aim to reduce the number of ports on the bioreactor to reduce the probability of contamination.

According to a first aspect of the invention, there is provided a liquid filtration system for perfusion of a cell culture liquid 100 comprising: a bioreactor 130 for holding cell culture liquid; a filter 140 configured to filter cell culture liquid passing therethrough; a perfusion pump 110 configured to move cell culture liquid between the bioreactor 130 and the filter 140; a liquid line 150 providing fluidic communication between the bioreactor 130, perfusion pump 110 and filter 140; and a bleed outlet 180 provided on the liquid line 150, the bleed outlet 180 configured to provide means to remove cell culture liquid selectively from the system 100 under the action of the perfusion pump 110.

With the liquid filtration system according to the present invention, both the filtering and bleed functions may be performed under the action of a single pump, thereby significantly reducing the complexity and cost of the components required. This also reduces the number of components that may need to be sterilised between uses, reducing the downtime such that a higher throughput is possible. Furthermore since the bleed outlet is provided on the liquid line between the pump and bioreactor there is no requirement for an additional port on the bioreactor and therefore the possibility of contamination of the cell culture held therein is significantly reduced. The system according to the present system may be automated in a straightforward manner by opening the bleed outlet to remove liquid under the normal action of the pump.

Certain examples of the invention provide a liquid filtration system for perfusion of a cell culture comprising a syringe pump comprising a gas chamber and a movable plunger, wherein the gas chamber has an aperture at a first end and the plunger forms a seal within the internal walls of the chamber; a liquid chamber having two openings, the openings positioned at opposite ends of the chamber and the first opening connected to the aperture of the gas chamber; a bioreactor in fluidic communication with the second opening of the liquid chamber; a filter arranged to filter liquid passing between the bioreactor and the liquid chamber, the filter comprising a permeate outlet for removing filtered liquid; wherein the plunger is movable in a reciprocating motion causing a corresponding movement of gas which drives liquid alternately between the liquid chamber and the bioreactor such that liquid passes through the filter and filtered liquid may be removed via the permeate outlet, the system further comprising a bleed outlet 180 configured to provide means to remove cell culture liquid selectively from the system 100 under the action of the perfusion pump.

BRIEF DESCRIPTION OF THE DRAWINGS

Embodiments of the invention will now be described, by way of example only, with reference to the accompanying drawings, in which.

DETAILED DESCRIPTION OF EMBODIMENTS OF THE INVENTION

In the description that follows and in the figures, certain examples of the invention are described. However, it will be appreciated that the invention is not limited to the examples that are described and that some examples may not include all of the features that are described below. It will be evident, however, that various modifications and changes may be made herein without departing from the broader spirit and scope of the invention as set forth in the appended claims.

Figure 1A:
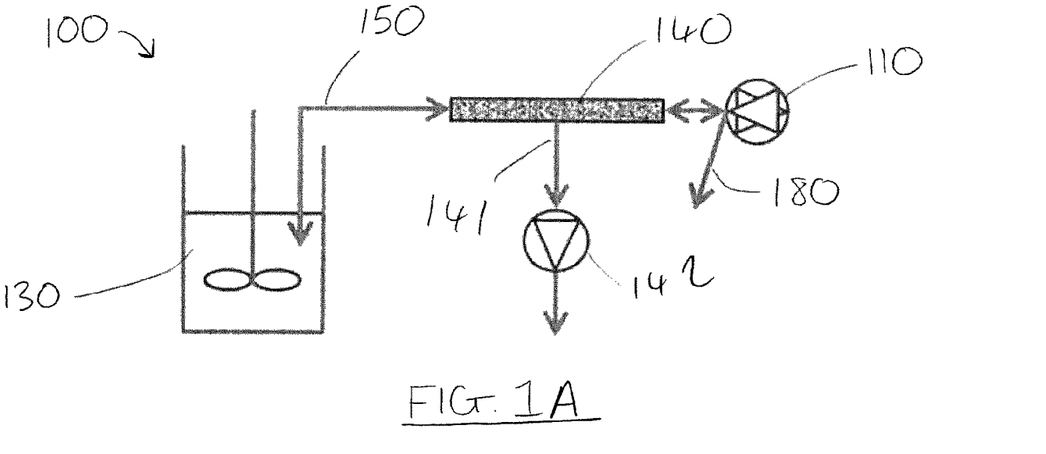
FIG. 1A schematically illustrates a first example of a liquid filtration system according to the present invention which may be operated in an alternating tangential filtration mode.
Figure 1B:
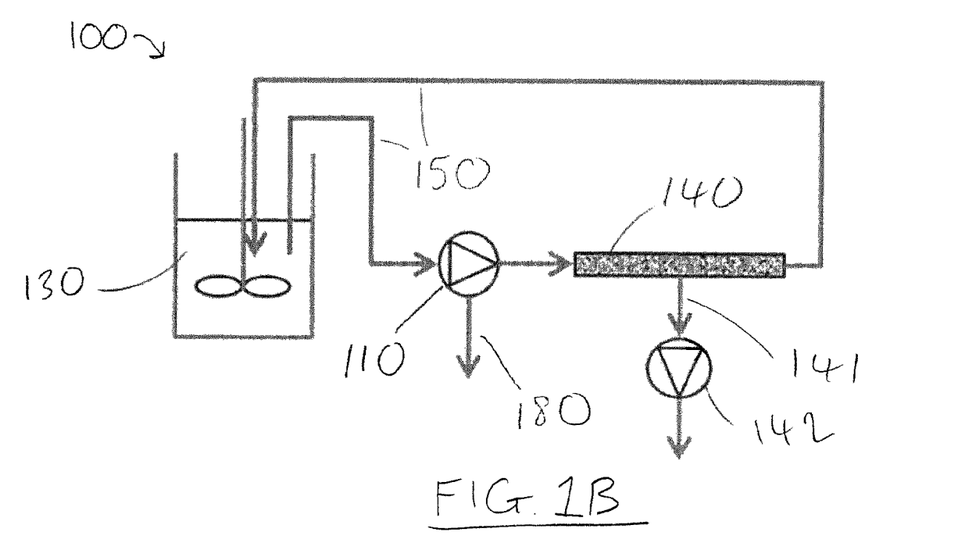
FIG. 1B schematically illustrates an example of a liquid filtration system according to the present invention which may be operated in a tangential flow filtration mode in which the liquid circulates in a loop.

FIGS. 1A and 1B illustrate the operating principle of a liquid filtration system 100 according to the present invention in an alternating tangential filtration (ATF) mode and a tangential flow filtration (TFF) mode respectively. The liquid filtration system 100 includes a perfusion pump 110, a bioreactor 130 and a filter 140, wherein the perfusion pump is configured to move the liquid from the bioreactor 140 through the filter 140 via a liquid line 150 which provides the required fluidic connection between the bioreactor 130, filter 140 and perfusion pump 110. The filtration system further includes a bleed outlet 180 which is provided on the liquid line 150. The bleed outlet 180 is configured to allow liquid to be selectively removed from the system 100 such that, under normal operation as liquid is moved along the liquid line under the action of the perfusion pump, the bleed outlet 180 may be opened such that liquid is pumped out of the system 100.

In the exemplary arrangements of FIGS. 1A and 1B, the bleed outlet 180 is provided as an outlet 180 on the perfusion pump 110 but it may be placed at any point on the liquid line 150. The examples shown in FIG. 1 also illustrate a permeate outlet 141 through which the filtered permeate may be removed from the filter 140. An external permeate pump 142 may be used to extract the filtered permeate through the outlet 141 and, as a known element separate from the perfusion and bleed functions, is outside of the current invention.

Unlike prior art systems which utilise a separate liquid line entering the bioreactor 130 such as a dip tube through which liquid is bled out of the system under the action of a second pump, the current invention only requires a single pump to provide both the perfusion of the liquid through the filter and the bleed function.

FIG. 1A illustrates a system according to the present invention arranged to provide ATF in which the action of the pump is alternated such that the direction of the liquid flow through the filter is periodically reversed. The liquid therefore moves reciprocally along the single liquid line 150 between the bioreactor 130 through the filter 140 to the pump 110 and back. In this example the bleed outlet is provided as an additional outlet on the perfusion pump 180 through which liquid may be selectively diverted out of the system 100 rather that back through the liquid line 150. This may be achieved for example by, when the pump direction is such as to effect movement of the liquid back to the bioreactor 130, opening a port on the pump 110 to direct the liquid out of the system.

FIG. 1B illustrates a system according to the present invention in which the components are arranged to provide TFF in which a loop is provided with the liquid line 150, around which the liquid may circulate between the bioreactor 130, filter 140 and pump 110 such that liquid moves in a single direction through the filter 140. Again, in this example the bleed outlet 180 is provided as an additional outlet on the perfusion pump 110. As described above, during normal use of the system the perfusion pump 110 acts to drive the liquid around the liquid line from the bioreactor 130 through the filter 140 and back to the bioreactor 130. When a bleed is required, for example to stabilise cell density in the cell culture, the bleed outlet 180 on the pump may be opened such that liquid is directed out of the system rather than continuing to circulate around the liquid line 150.

Figure 2:
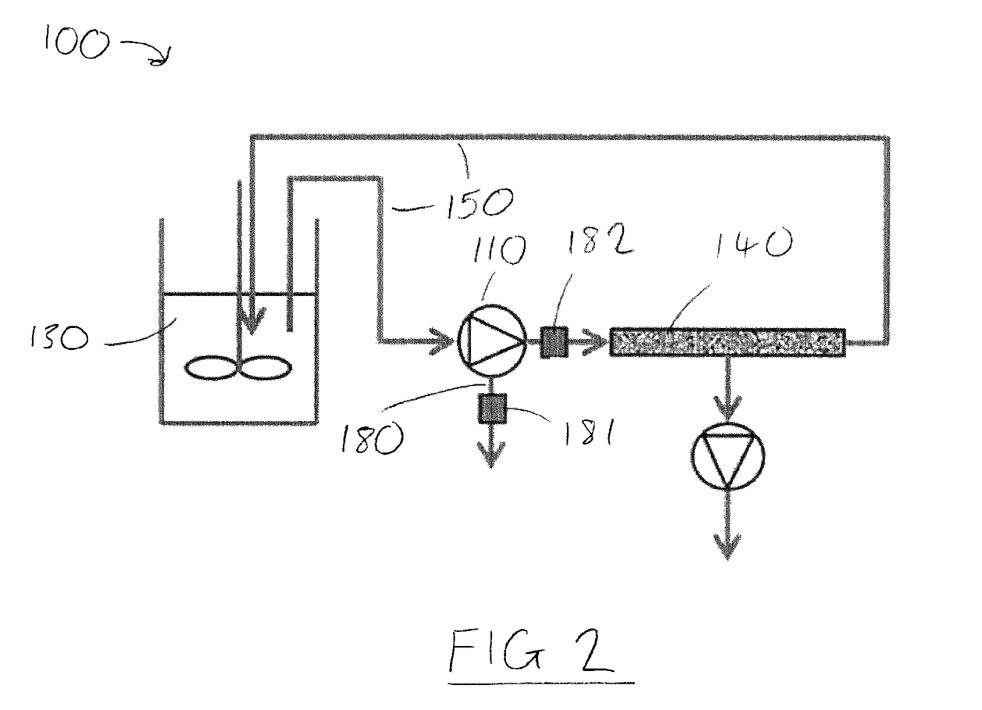
FIG. 2 schematically illustrates an example of the liquid filtration according to the present invention which incorporates two valves to provide the bleed outlet.

FIG. 2 schematically illustrates one straightforward means in which the bleed function can be controlled; illustrated in this figure for the case of the exemplary TFF system of FIG. 1B. In this example, a first pinch valve 181 is provided on the bleed outlet 180 and a second pinch valve is provided on a portion of the liquid line 150 immediately following the perfusion pump 110 in the direction of liquid flow. During normal operation of the system 100 the first pinch valve 181 is closed and the second pinch valve 182 is open such that the perfusion pump acts to drive liquid around the liquid line 150 circuit such that liquid passes through the filter 140 and permeate may be removed. When liquid needs to be removed from the system, for example to reduce cell density, a bleed operation may be performed by closing the second pinch valve 182 on the liquid line and opening the first pinch valve 181 on the bleed outlet such that liquid is diverted out of the system through the bleed outlet 180 under the normal action of the perfusion pump 110. The liquid flow through the perfusion recirculation loop to and from the bioreactor 130 and the flow though the bleed outlet 180 can therefore be controlled independently.

Figure 3:
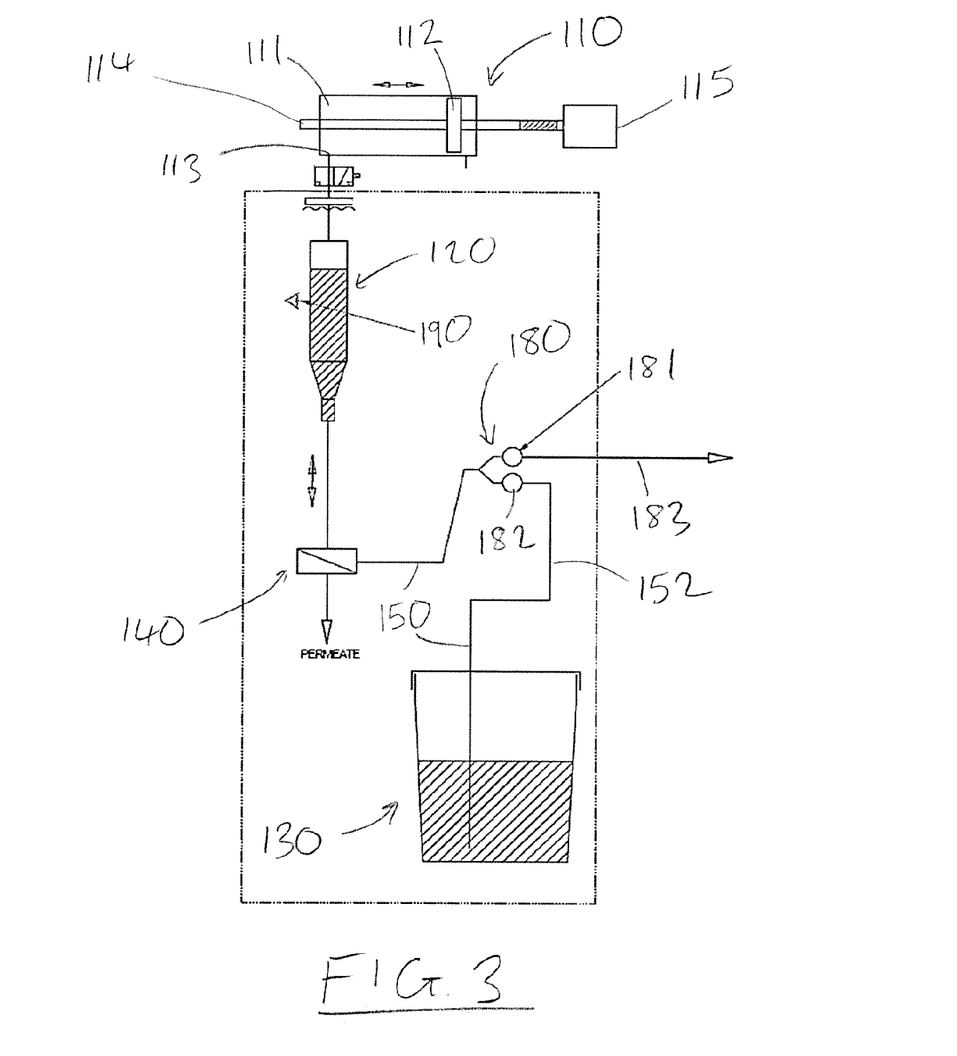
FIG. 3 schematically illustrates a further example of the liquid filtration system according to the present invention which incorporates a syringe pump and bleed outlet between the filter and bioreactor.

FIG. 3 illustrates a further example of a filtration system according the present invention which is configured to provide an ATF filtration process. In this arrangement the liquid is driven by a syringe pump 110 comprising a plunger 112 and gas chamber 111, wherein the plunger forms a seal with the internal walls of the chamber 111 and is configured to move through the chamber 111 so as to expel air though an aperture 113 positioned at one end. The plunger 12 may be mounted on a piston rod 114 which is positioned along an elongate axis of the chamber 111 and is driven by a motor 115 to provide the required alternating motion. The aperture at one end of the gas chamber 111 is in fluidic communication with a liquid chamber 120 which, in turn, is connected with the filter 140 and bioreactor 130. Therefore the alternating movement of gas driven by the movement of the plunger 112 is transferred to the liquid held in the liquid chamber 120 so as to drive it along the liquid line 150 alternately between the bioreactor 130 and liquid chamber 120, such that it passes through the filter 140. The direction of the liquid within the system therefore alternates with the movement of the plunger 112. Movement of the plunger 112 towards the aperture 113 causes gas to enter the liquid chamber, driving liquid through the filter to the bioreactor and movement of the plunger 112 away from the aperture causes gas to evacuate the liquid chamber 120 causing liquid to move from the bioreactor 130 through the filter 140 to fill the liquid chamber 120.

Unlike the previous examples, rather than being provided on the pump 110 in the system of FIG. 3, the bleed outlet 180 is provided on the liquid line 150 between the filter 140 and bioreactor 130. The bleed outlet 180 may be provided simply by a valved junction in the liquid line 150 between the filter 140 and the bioreactor 130. The liquid line split into a first line 152 returning to the bioreactor 130 and a second, bleed line 183 directed out of the system. The bleed function may again be achieved simply by a first 181 and second 182 pinch valve provided on the bleed line 183 and the return portion of the liquid line 152 respectively. The opening and closing of the pinch valves 181, 182 may be coordinated with the action of the perfusion pump. Under normal use of the system for filtering the liquid, the first pinch valve 181 is closed and the second pinch valve 182 is open such that, under the action of the pump 110, liquid moves along the liquid line 150 between the liquid chamber 120 and bioreactor 130 through the filter 140. When it is necessary to remove liquid from the system, the first pinch valve 181 on the bleed line 183 is opened and the second pinch valve 182 on the return portion 152 liquid line 150 is closed. When the plunger 112 moves towards the aperture 113, liquid is driven from the liquid chamber 120 along the liquid line 150 and bleed line 183 and exits the system. The valves may be coordinated with the action of the pump such that the bleed line 183 is opened (and return line 152 closed) only as the plunger 112 of the pump moves towards the aperture 113. Like all examples of the present invention, the coordinated control of the bleed outlet 180 and pump 110 may be provided manually by a user or automated by configuration of an external control system.

Unlike prior art systems, in which a separate pump is required to provide the bleed function, again in this arrangement there is no need to provide an additional pump or external cell removal device dedicated to bleeding the system.

Figure 4:
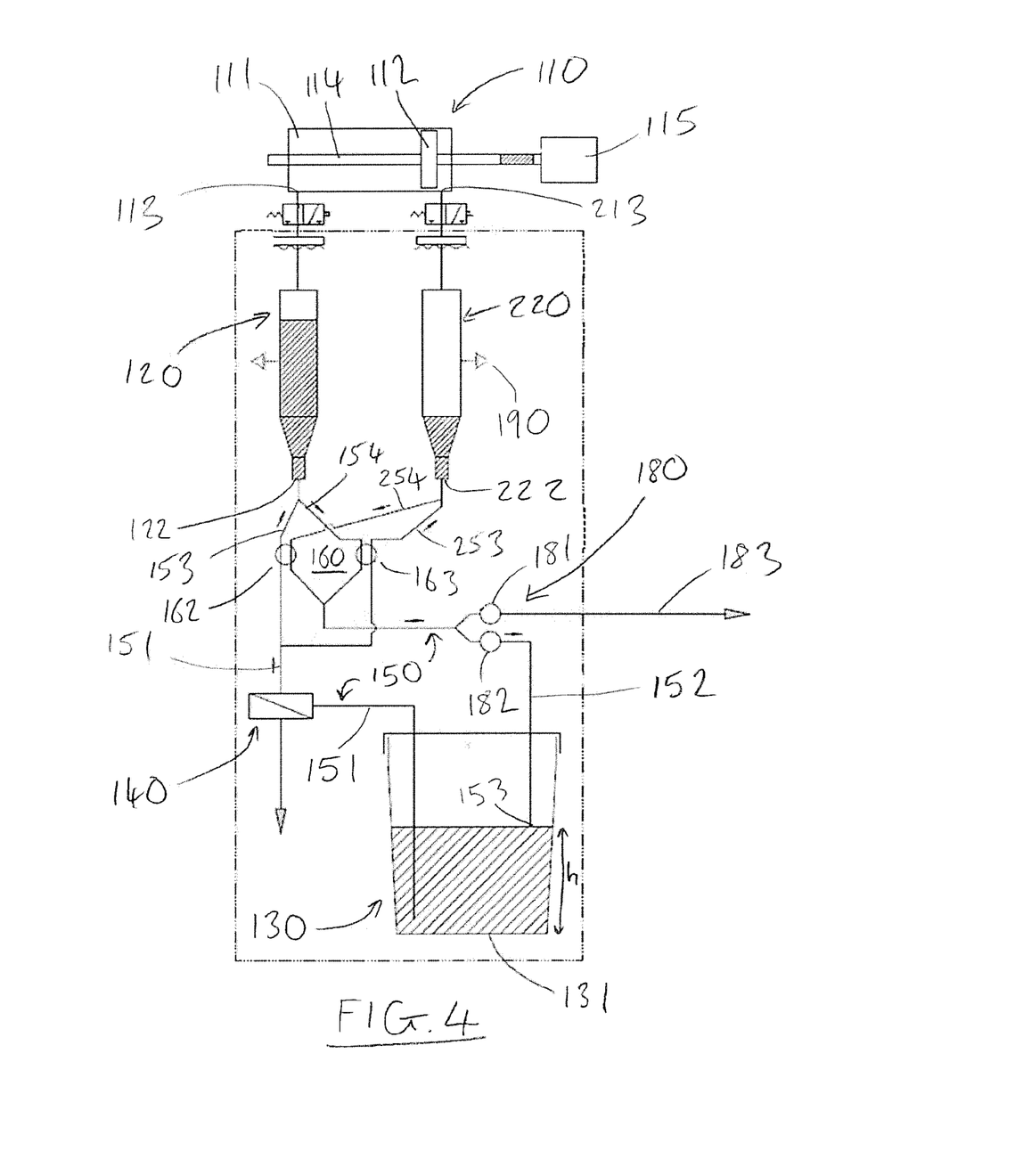
FIG. 4 schematically illustrates a further example of the liquid filtration system according to the present invention which incorporates a pinch valve and a bleed outlet on a liquid return line.

FIG. 4 illustrates a further exemplary filtration system configured to provide TFF according to the present invention. The system of FIG. 4 incorporates a syringe pump 110 similar to the arrangement of FIG. 3 but differing in that a second aperture 213 is positioned in the gas chamber 111 at an opposing end to that of the first aperture 113. The piston rod 114 is a "through rod" running axially through the chamber 111, wherein the plunger 112 is placed on a middle portion of the rod 114 such that it moves alternately through the chamber 111 between the opposing first and second ends. Since the first 113 and second 213 apertures are positioned near the opposing ends of the chamber 111, gas is expelled through one aperture whilst being drawn into the other aperture. The first and second apertures 113, 213 may be connected to a first 120 and second 220 liquid chamber respectively, each connected in a manner similar to that described with reference to FIG. 3. The motion of the plunger 112 therefore causes liquid held in one liquid chamber 120, 220 to be expelled through the opening 122, 222 whilst liquid is drawn through the opening of the other liquid chamber, into the chamber 220, 120.

FIG. 4 further illustrates how liquid chambers 120, 220 may be connected to the filter 140 and bioreactor 130 to provide continuous perfusion in a TFF arrangement. There is a junction in the liquid line leaving the opening 122, 222 of each chamber such that each splits into two lines, an inlet line 153, 253 connected to the main liquid uptake line 151 and an outlet line 154, 254 connected to the main liquid return line 152. The flow of liquid between the liquid chambers and the remainder of the system is controlled by opening and closing the inlet lines 153, 253 and outlet lines 154, 254 using the valve system 160. In this example the valve system is provided by a number of flow control valves 162, 163 (for example further pinch valves) to control the flow of liquid within the system. As the plunger 112 moves to the right of the chamber 111, the first flow control valve 162 is open and the second flow control valve 163 is closed. Liquid is then drawn from the bioreactor through the uptake line 151 via the filter 140 and into the first liquid chamber through the inlet 153.

Simultaneously liquid is expelled though the outlet 254 of the second liquid chamber which connects to the liquid return line 152, returning the liquid to the bioreactor 130. The first flow control valve 162 is then closed and the second flow control valve 163 is opened while the plunger 112 moves to the left towards the first end of the chamber 111. Accordingly liquid is drawn from the bioreactor 130, through the filter 140 and into the second liquid chamber 220 via the inlet line 253. Simultaneously liquid is expelled through the outlet line 154 of the first liquid chamber 120 and returned to the bioreactor via the return line 152. By synchronising the operation of flow control valves 162 and 163 with the motion of the syringe pump 110, effectively pulse-free continuous TFF can be achieved.

Similarly to the arrangement to FIG. 3, in order to facilitate bleeding of the system a valved junction is provided in the return line 152 which connects the liquid chambers 120, 220 with the bioreactor. As described above, a first branch in the return line 152 is connected so as to return liquid to the bioreactor 130 under normal operation, the other directs fluid out of the system through the bleed line 183. The branches in the return line 152 may be provided with first and second pinch valves 181, 182 which can open and close the lines to control the bleed function. During normal operation, a first bleed line pinch valve 181 is closed and a second, return line pinch valve 182 is open. When bleeding cells, the bleed line pinch valve 181 is opened and return line pinch valve 182 is closed such that the action of the syringe pump pushes liquid out of the liquid chamber and through the bleed outlet 183, rather than being returned to the bioreactor vessel 130. Unlike the example of FIG. 3, in the arrangement of FIG. 4 cell bleeding can be carried out regardless of syringe pump direction since both sides of the gas chamber 111 are connected to liquid chamber 120, 220 such that liquid is driven along the return line 152 for both directions of motion of the plunger 112.

The arrangement of FIG. 4 also provides further functionality. During perfusion, liquid is constantly being drawn out of the system (the permeate), and is replenished by the addition of media feed. Both pumping rates are controlled, but over the long periods of an experiment, the volume of culture in the bioreactor 130 may vary if the permeate and pump flow rates are not identically matched. One method of ensuring that culture volume does not drop is to constantly over-feed media into the bioreactor 130, and periodically bleed cells out of the bioreactor 130. This may be achieved with the arrangement of FIG. 4 by firstly reversing the sequencing of the flow control valves 162, 163 with respect to the motion of the plunger 111. By configuring the flow control valves 162, 163 in this way, liquid is extracted from the bioreactor 130 through the liquid return line 152 into the first and second liquid chambers 120, 220 under the action of the perfusion pump 110. Following removal of liquid from the bioreactor 130 through the liquid return line 152, the first pinch valve 181 can be opened and the second pinch valve 182 closed while the normal sequencing of the flow control valves 162, 163 and perfusion pump 110 is resumed such that liquid is moved out of the system through the bleed lines 183 under the action of the perfusion pump 110.

By providing a return line 152 (in the form of a dip tube for example) which has a fixed height h above the internal base 131 of the bioreactor 130, liquid can be extracted through the return line 152 until it reaches this known level h within the bioreactor 130. Alternatively the length of the return line within the bioreactor may be varied such that the distance h between the end 153 of the return line 152 and the base of the bioreactor 131 can be adjusted. In this way, when removing liquid from the bioreactor 130 through the return line 152 as described above, the liquid level may be adjusted to a known height h within the bioreactor 130.

Figure 5:
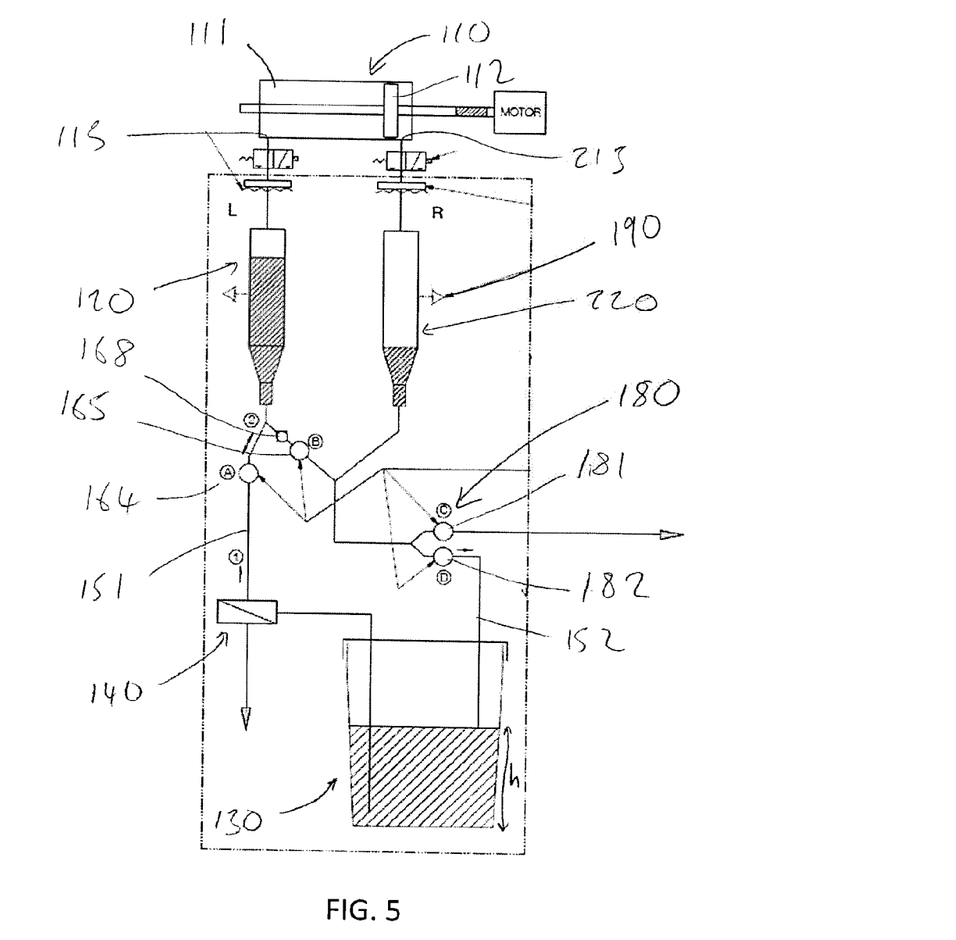
FIG. 5 schematically illustrates a further example of the liquid filtration system according to the present invention which is configured to provide ATF and incorporates a bleed outlet on a liquid return line from a second liquid chamber.

FIG. 5 illustrates a further embodiment, which utilises a modified version of the arrangement of FIG. 4, configured to provide ATF rather than TFF. As with the latter arrangement, the syringe pump 110 has first and second apertures 113, 213 at opposing ends of the gas chamber 111, the apertures connected to first 120 and second 220 liquid chambers respectively. In this arrangement the first liquid chamber 120 is connected to the bioreactor 130 via the filter 140 via a liquid line 151 through which the liquid is driven alternatingly to provide ATF. The second liquid chamber 220 is connected via the bleed outlet 180 to the bioreactor 130. Using this arrangement, two differing bleed processes may be implemented.

Firstly, integrated cell bleeding may be provided during filtration wherein, upon expulsion of the liquid from liquid chamber 120, the first flow control valve 164 is closed and the second flow control valve is opened while the bleed pinch valve 181 is open and the return line pinch valve 182 is closed, such that liquid is directed out of the bleed outlet 183. Alternatively, independent bleeding to level may be achieved, utilising the second liquid chamber 220 to simply draw the liquid from the bioreactor 130 into the second liquid chamber before expelling through the bleed outlet 180 and repeating until the required level is reached.

In more detail, ATF is provided by closing the second flow control valve 165, opening the first flow control valve 164 and moving the plunger 112 to alternatingly draw the liquid from the bioreactor 130 through the filter 140 into the first liquid chamber 120 before returning it along the liquid line 151 through the filter and back into the bioreactor 130. To provide the integrated bleed function, upon expulsion of the liquid from the first liquid chamber, the liquid is directed out of the bleed outlet by closing pinch valves 164 and 182, opening valves 165 and 181, then emptying the first liquid chamber 120 via a check valve 168. The check valve 168 minimises the "dead volume" of ejected cells remaining in the branch of tubing, and prevents any "back flow" of ejected cells which might contaminate the rest of the cell culture flowing into and out of the first liquid chamber 120 from the perfusion filter 140. The check valve is not used to control flow direction for ATF perfusion functionality.

To provide bleeding-to-level, the dip tube 152 (which has the additional function of acting as the return line 152 when the arrangement is configured for TFF) is used. The second liquid chamber 220 draws cell culture up from the shortened dip tube 152 via the return line valve 182 being open (and valves 165 and 181 being closed). The second liquid chamber 220 is then emptied by closing valve 182 and opening bleed valve 181. The process is repeated until no further liquid can be withdrawn up the dip tube because the level has dropped below the end of the tube. The amount of liquid in the bioreactor may therefore be regulated and returned to a liquid level of height h within the bioreactor 130.

Examples of the present invention may further include one or more sensors 190 which are configured to sense one or more parameters of the system. Although the sensors 190 in FIGS. 3 and 4 are external sensors configured to sense the liquid level within the one or more liquid chambers 120, 220, sensors configured to sense other parameters such as cell density, cell viability and pressure may additionally be incorporated. As described above, control of the motion of the plunger, the motor and the sequencing of the flow control and pinch valves may be performed manually by a user or automated by a control unit. The control unit may allow programming of the required phases of ATF, TFF, cell bleeding and liquid level control. Control of the various operations described above may also be automated with the various functions controlled in response to data sensed by the sensors. For example, when sensed data suggests cell density is rising above a predetermined threshold the control system can start cell bleeding to reduce cell density until a predetermined acceptable level is reached, as determined by a sensor. The bleed outlet may be controlled such that the flow of liquid out of the system may be continuous or periodic.

In all of the above described examples of the present invention, the tubing forming the liquid lines together with the pinch valves may be provided within a replaceable cartridge. For example in the embodiments of FIGS. 4 and 5 the labware requires six pieces of tubing to be routed correctly through four pinch valves. To eliminate the possibility of the operator getting this wrong, and to make operator's task very easy, the tubing is pre-loaded into a disposable cartridge which is an integral part of the labware. The operator only has to load the cartridge (a simple task taking a few seconds) to robustly and correctly make all the necessary connections.

In all of the above described examples of the present invention, the entire product-contact path (that is, components which are direct contact with cell culture) may be single-use disposable items comprising the labware. The labware is designed to minimise the skill and time required to connect a bioreactor 130 with a perfusion filter 140 to the machine which drives the pump (while maintaining sterility) to fulfil all the environmental, gassing, feeding, stirring, circulation and sensing functions required to perform the process. The pump 110 itself may then be a fixed part of the machine, not requiring to be cleaned or sterilised, and may be connected to the labware via integrated sterile filters in the labware. The cell culture does not flow through a mechanical pump (eg, diaphragm, impeller or peristaltic, which can damage cells)—the flow is achieved by sucking the cell culture out of the bioreactor 130, through the perfusion filter 140, and then "blown" back into the reactor 130, either back through the filter 140 ("ATF"), or via a separate return line 152 ("TFF"). The only contact with cell culture is sterile tubing and other single-use disposable plastic components and clean, filtered air.

For ATF or TFF, only one liquid chamber is required for normal perfusion functions. However, by using a second chamber, a "quasi-continuous" flow can be achieved for TFF—while cell culture is being sucked out of the bioreactor 130 through the perfusion filter 140 into one liquid chamber 120, cell culture from the previous cycle can be returned to the bioreactor 130 from the second liquid chamber 202.

Typically, perfusion experiments can last for 30 to 60 days, with cell culture continuously flowing in and out of the liquid chambers. Even though the material of the chambers, for example polypropylene, has low surface energy, and cell culture does not easily bind to the surfaces, over the long period of the experiment, cell-culture can start building up on the walls of the chambers. This can reduce the volume in the chambers to an unacceptably low level, and/or could potentially have a detrimental effect on the cells flowing into the chamber. A fluorination process may be used on the liquid chambers which effectively changes the surface polymer to PTFE, thus reducing cell-binding on the liquid chamber wall.

With the liquid filtration system according to the present invention, a simple low cost arrangement is provided for facilitating cell bleeding. Unlike prior art systems which require an additional pump for removing cell culture from a bioreactor, the present invention uses an arrangement in which the action of the perfusion pump may be harnessed to extract liquid from the system. This reduces the cost and complexity associated with incorporating an additional pump and further reduces the chances of malfunction and the downtime needed to sterilise equipment between runs.

The system according to the present invention does not require an additional port to the bioreactor, unlike prior art systems, so the probability of contamination is further reduced. Furthermore, the degree of user involvement or automation required to control both filtration and bleed functions is reduced since these may both be provided by control of the single pump and associated valves. Arrangements of the present invention also provide means to regulate the liquid level within the bioreactor, adding additional functionality with a reduced number of components.

The invention claimed is:

1. A liquid filtration system for perfusion of a cell culture comprising:
   a bioreactor for holding a cell culture liquid;
   a filter configured to filter cell culture liquid passing therethrough;
   a perfusion pump configured to move cell culture liquid between the bioreactor and the filter;
   a liquid line providing fluidic communication between the bioreactor, perfusion pump and filter; and
   a bleed outlet provided on the liquid line as an additional outlet in the perfusion pump, the bleed outlet configured to provide means to remove cell culture liquid selectively from the system under the action of the perfusion pump.

2. The liquid filtration system of claim 1 wherein the bleed outlet further comprises
   a first pinch valve configured to selectively open and close the bleed outlet.

3. The liquid filtration system of claim 2 further comprising a second, associated pinch valve, the second pinch valve configured to close the liquid line when the first pinch valve is open.

4. The liquid filtration system of claim 1 further comprising one or more sensors configured to determine one or more parameters of a liquid in the system.

5. The liquid filtration system of claim 4 wherein the parameters sensed by the one or more sensors include one or more of the following:
   liquid level, pressure, cell density, cell viability.

6. The liquid filtration system of claim 1 wherein the liquid line comprises
   a liquid uptake line through which cell culture liquid is extracted from the bioreactor; and
   a liquid return line through which cell culture liquid is returned to the bioreactor wherein
   the liquid uptake line and liquid return line together provide a circuit connecting the bioreactor, filter and perfusion pump, around which a cell culture liquid flows under the action of the perfusion pump during use.

7. The liquid filtration system of claim 6 wherein the end of the liquid return line within the bioreactor is separated from the base of the bioreactor by a specified height (h).

8. The liquid filtration system of claim 7 wherein the perfusion pump is configured to selectively reverse the circulation of cell culture liquid within the system by removing cell culture liquid from the bioreactor via the liquid return line and directing the liquid out of the bleed outlet, thereby regulating the level of the liquid in the bioreactor to the specified height (h).

9. A method for removing cell culture liquid from a liquid filtration system, the system comprising:
   a bioreactor for holding cell culture liquid;
   a filter configured to filter cell culture liquid passing therethrough;

a perfusion pump configured to move cell culture liquid between the bioreactor and the filter;

a liquid line providing fluidic communication between the bioreactor, perfusion pump and filter; and a bleed outlet provided on the liquid line as an additional outlet in the perfusion pump, the bleed outlet configured to provide means to remove cell culture liquid selectively from the system; the method comprising:

operating the perfusion pump such that cell culture liquid is moved through the filter via the liquid line;

opening the bleed outlet such that the cell culture liquid is removed from the liquid line under the action of the perfusion pump;

closing the bleed outlet after a desired amount of cell culture liquid has been removed from the system.

10. The method of claim 9 wherein the system further comprises a first pinch valve configured to open and close the bleed outlet;

a second pinch valve configured to open and close the liquid line; the method further comprising:

opening the first pinch valve and closing the second pinch valve such that cell culture liquid is directed out of the bleed outlet.

11. The method of claim of claim 10 wherein the system further comprises:

a liquid uptake line through which cell culture liquid is extracted from the bioreactor under the action of the perfusion pump; and a liquid return line through which cell culture liquid is returned to the bioreactor under the action of the perfusion pump, the end of the liquid return line within the bioreactor being separated from the base of the bioreactor by a specified height (h); wherein the liquid uptake line and liquid return line together provide a circuit connecting the bioreactor, filter and perfusion pump, around which a liquid flows under the action of the perfusion pump during use;

the method further comprising:

reversing the action of the perfusion pump when second pinch valve is open such that cell culture liquid is extracted from the bioreactor by the liquid return line until the level of liquid has reduced to the specified height (h);

closing the second pinch valve and opening the first pinch valve; and resetting the action of the perfusion pump such that liquid is diverted out of the bleed outlet under the action of the perfusion pump.

12. The method of claim 9, the liquid filtration system further comprising:

one or more sensors configured to sense one or parameters associated with the liquid in the system; the method further comprising:

opening and closing the bleed outlet according to the parameters sensed by the one or more sensors.

* * * * *